US012678610B2

(12) United States Patent
Johnson et al.

(10) Patent No.: US 12,678,610 B2
(45) Date of Patent: Jul. 14, 2026

(54) VALVE ASSEMBLY FOR SEALING AN INSTRUMENT CHANNEL ON A ROBOTIC SURGICAL SYSTEM

(71) Applicant: EndoQuest Robotics, Inc., Houston, TX (US)

(72) Inventors: Graham Johnson, Seattle, WA (US); Yongman Park, Houston, TX (US); Sungwoo Cho, Richmond, TX (US); Daniel Kim, Quincy, MA (US); Raymond Lee, Houston, TX (US); Dongsuk Shin, Houston, TX (US); Perry A. Genova, Chapel Hill, NC (US)

(73) Assignee: EndoQuest Robotics, Inc., Houston, TX (US)

( * ) Notice: Subject to any disclaimer, the term of this patent is extended or adjusted under 35 U.S.C. 154(b) by 255 days.

(21) Appl. No.: 18/535,425

(22) Filed: Dec. 11, 2023

(65) Prior Publication Data

US 2025/0186757 A1    Jun. 12, 2025

(51) Int. Cl.
*A61M 39/22* (2006.01)
*A61B 34/30* (2016.01)

(52) U.S. Cl.
CPC .............. *A61M 39/22* (2013.01); *A61B 34/30* (2016.02); *A61B 2034/301* (2016.02)

(58) Field of Classification Search
CPC .. A61B 2034/301; A61B 34/30; A61M 39/06; A61M 39/22
See application file for complete search history.

(56) References Cited

U.S. PATENT DOCUMENTS

| | | | | |
|---|---|---|---|---|
| 2004/0260244 A1* | 12/2004 | Piechowicz | ........ | A61B 17/3462 |
| | | | | 606/167 |
| 2006/0020281 A1* | 1/2006 | Smith | ................ | A61B 17/3462 |
| | | | | 606/167 |
| 2007/0016174 A1* | 1/2007 | Millman | ............... | A61M 1/743 |
| | | | | 606/1 |
| 2008/0234631 A1* | 9/2008 | Reis | ........................ | A61B 34/37 |
| | | | | 604/122 |
| 2020/0397456 A1 | 12/2020 | Kim et al. | | |
| 2021/0275266 A1 | 9/2021 | Kim et al. | | |
| 2022/0133352 A1* | 5/2022 | Morrissette | ............ | A61B 90/30 |
| | | | | 600/203 |
| 2022/0354524 A1 | 11/2022 | Kim et al. | | |
| 2023/0210618 A1 | 7/2023 | Kim et al. | | |
| 2023/0210621 A1 | 7/2023 | Noh et al. | | |
| 2023/0248419 A1 | 8/2023 | Cho et al. | | |

(Continued)

*Primary Examiner* — Scott Luan
(74) *Attorney, Agent, or Firm* — Troutman Pepper Locke LLP; Scott D. Wofsy; Michael J. Pollack

(57)    ABSTRACT

A valve assembly is disclosed for sealing an instrument channel of a robotic surgical device, which includes a valve body having a longitudinal axis extending therethrough from a proximal end portion of the valve body to a distal end portion of the valve body, and defining an axial bore including an interior valve chamber formed in the proximal end portion of the valve body, a valve seal situated within the interior valve chamber of the valve body for sealing the instrument channel of the robotic surgical device, and an engagement mechanism operatively associated with the distal end portion of the valve body for detachably connecting the valve assembly to the instrument channel of the robotic surgical device.

19 Claims, 5 Drawing Sheets

(56)     References Cited

U.S. PATENT DOCUMENTS

| 2023/0248450 | A1 | 8/2023 | Ravi et al. |
|---|---|---|---|
| 2023/0248457 | A1 | 8/2023 | Lee et al. |
| 2023/0255702 | A1 | 8/2023 | Park et al. |
| 2023/0285090 | A1 | 9/2023 | Lee et al. |
| 2023/0285098 | A1 | 9/2023 | Lee et al. |
| 2023/0285099 | A1 | 9/2023 | Lee et al. |
| 2023/0355221 | A1 | 11/2023 | Shin et al. |
| 2023/0363842 | A1 | 11/2023 | Choi et al. |
| 2023/0363847 | A1 | 11/2023 | Lee et al. |
| 2024/0058079 | A1 | 2/2024 | Kim et al. |

* cited by examiner

VALVE ASSEMBLY FOR SEALING AN INSTRUMENT CHANNEL ON A ROBOTIC SURGICAL SYSTEM

BACKGROUND OF THE DISCLOSURE

1. Field of the Invention

The subject disclosure is directed to robotic surgical systems, and more particularly, to a disposable valve assembly for sealing an instrument channel of a robotically controlled medical device.

2. Description of Related Art

In robotically assisted minimally invasive surgery, surgical procedures are performed by a surgeon controlling a robotically controlled medical device. The robotically controlled medical device will often have one or more working channels for guiding surgical instruments and videoscopes to an insufflated surgical site.

These working channels are sealed to prevent insufflation gases from escaping from the surgical site regardless of whether an instrument is installed. Typically, the seals on a working channel are made from compliant elastomeric materials, and they are not removable or replaceable. Therefore, such seals are subject to wear and failure over time from friction and repeated expansion and contraction caused by instruments being passed therethrough.

It would be advantageous to provide a disposable sealing assembly for a working channel of a robotically controlled medical device that can be easily installed for use during a surgical procedure and subsequently removed from the working channel after the surgical procedure has been completed without any tools. Such a sealing assembly would overcome the disadvantages associated with permanently installed working channel seals known in the art.

SUMMARY OF THE DISCLOSURE

The subject disclosure is directed to a new and useful valve assembly for sealing an instrument channel of a robotic surgical device. The valve assembly includes a valve body having a longitudinal axis extending therethrough from a proximal end portion of the valve body to a distal end portion of the valve body, and defining an axial bore including an interior valve chamber formed in the proximal end portion of the valve body. The valve assembly further includes a valve seal situated within the interior valve chamber of the valve body for sealing the instrument channel of the robotic surgical device, and an engagement mechanism operatively associated with the distal end portion of the valve body for detachably connecting the valve assembly to the instrument channel of the robotic surgical device.

In an embodiment of the subject disclosure, the valve seal is a cross-slit valve seal adapted to seal the instrument channel of the robotic surgical device in the absence of an inserted instrument. The valve assembly further includes a backup seal situated within the interior valve chamber of the valve body proximal to the valve seal for sealing against instrument insertion. In an embodiment of the subject disclosure, the backup seal is a septum seal adapted to seal against instrument insertion. The valve assembly further includes a proximal end cap operatively associated with the proximal end portion of the valve body for securing the backup seal and the valve seal within the interior chamber of the valve body.

In an embodiment of the subject disclosure, the engagement mechanism is preferably configured as a bayonet-type engagement mechanism for detachably engaging the valve assembly to the instrument channel of the robotic surgical device. The bayonet-type engagement mechanism includes a pair of diametrically opposed locking tabs that extend radially inwardly into the axial bore of the valve body for cooperating with a pair of corresponding engagement slots formed on a connector of the instrument channel of the robotic surgical device. The bayonet-type engagement mechanism further includes a spring-biased crown configured for axial movement between a first position biased distally relative to the distal end portion of the valve body and a second position retracted proximally relative to the distal end portion of the valve body. The spring-biased crown is biased distally by a wave spring positioned between the distal end portion of the valve body and the spring-biased crown, and a distal end cap is provided for capturing the spring biased crown relative to the distal end portion of the valve body.

The subject disclosure is also directed to a disposable valve assembly for sealing an instrument channel of a robotic surgical device, which includes a valve body having a longitudinal axis extending therethrough from a proximal end portion of the valve body to a distal end portion of the valve body, and defining an axial bore including an interior valve chamber in the proximal end portion of the valve body, a cross-slit valve seal situated within the interior valve chamber of the valve body for sealing the instrument channel of the robotic surgical device, a septum seal situated within the interior valve chamber of the valve body proximal to the cross-slit valve seal for sealing against instrument insertion, and a bayonet-type engagement mechanism operatively associated with the distal end portion of the valve body for detachably connecting the valve assembly to a connector of the instrument channel of the robotic surgical device.

The subject disclosure is further directed to a disposable valve assembly for sealing an instrument channel of a robotic surgical device, which includes a valve body having a longitudinal axis extending therethrough from a proximal end portion of the valve body to a distal end portion of the valve body, and defining an axial bore including an interior valve chamber in the proximal end portion of the valve body, a valve seal situated within the interior valve chamber of the valve body for sealing the instrument channel of the robotic surgical device, and a bayonet-type engagement mechanism operatively associated with the distal end portion of the valve body for detachably connecting the valve assembly to a connector of the instrument channel of the robotic surgical device and including a pair of diametrically opposed locking tabs that extend radially inwardly into the axial bore of the valve body for cooperating with a pair of corresponding engagement slots formed on the connector of the instrument channel of the robotic surgical device.

These and other features of the subject disclosure will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the sealing valve assembly of the subject disclosure without undue experimentation, preferred embodiments thereof will be described in detail herein below with reference to the figures wherein.

DETAILED DESCRIPTION OF THE PREFERRED EMBODIMENTS

Figure 1:
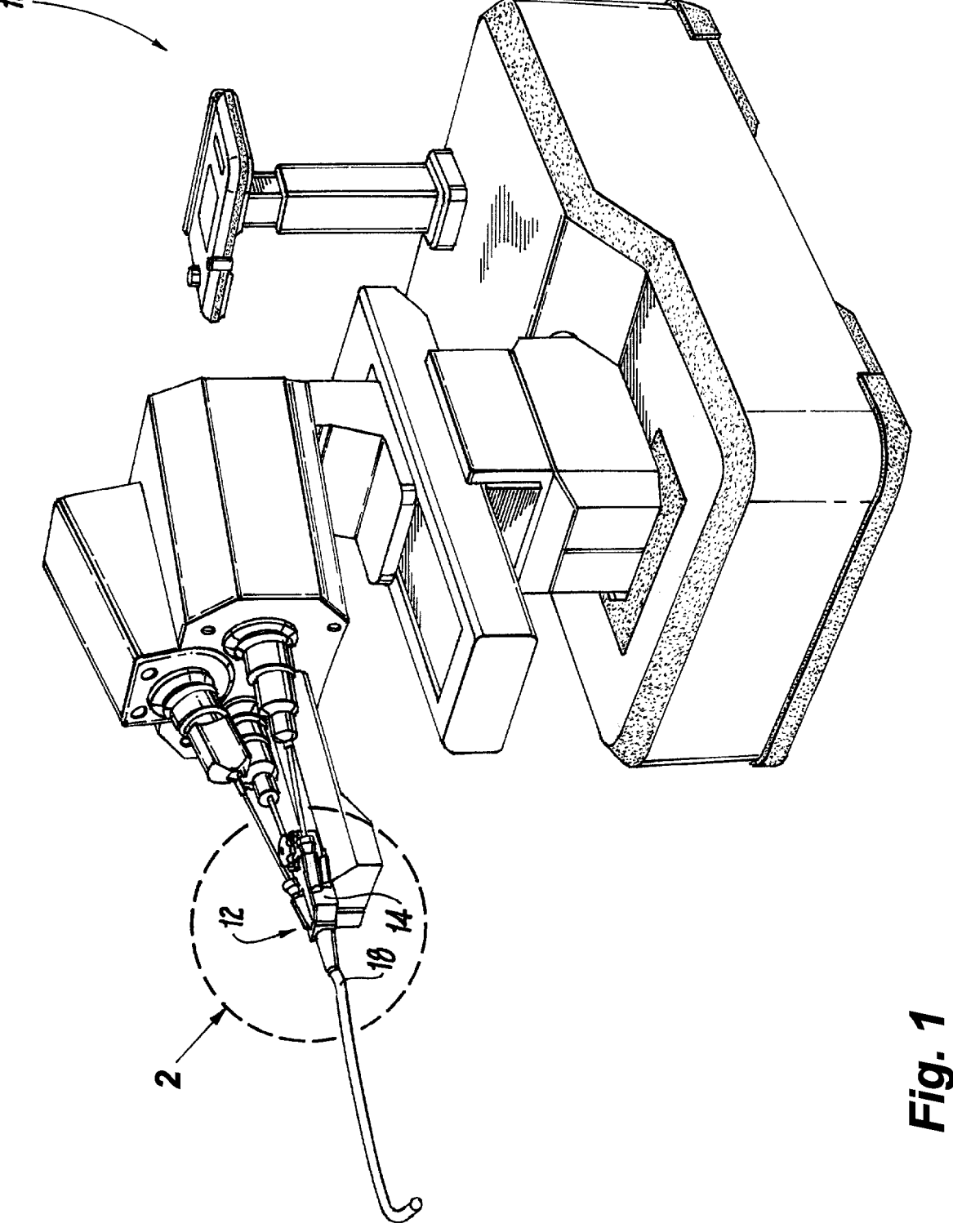
FIG. 1 is perspective view of a robotic surgical system that includes a robotic surgical device with instrument channels that are sealed with the valve assembly of the subject disclosure.

Referring now to the drawings, wherein like reference numerals identify similar structural elements or features of the subject disclosure, there is illustrated in FIG. 1 a robotic surgical device 10 in the form of a mobile patient console that is adapted for use during the performance of a surgical procedure. A mobile patient console of this type is disclosed in commonly assigned U.S. Patent Application Publication 2023/0285098, the disclosure of which is incorporated herein by reference in its entirety. The robotic surgical device 10 includes a videoscope and overtube assembly 12. A videoscope and overtube assembly of this type is disclosed in commonly assigned U.S. Patent Application Publication 2023/0210618, the disclosure of which is incorporated herein by reference in its entirety.

Figures 2, 3, 4:
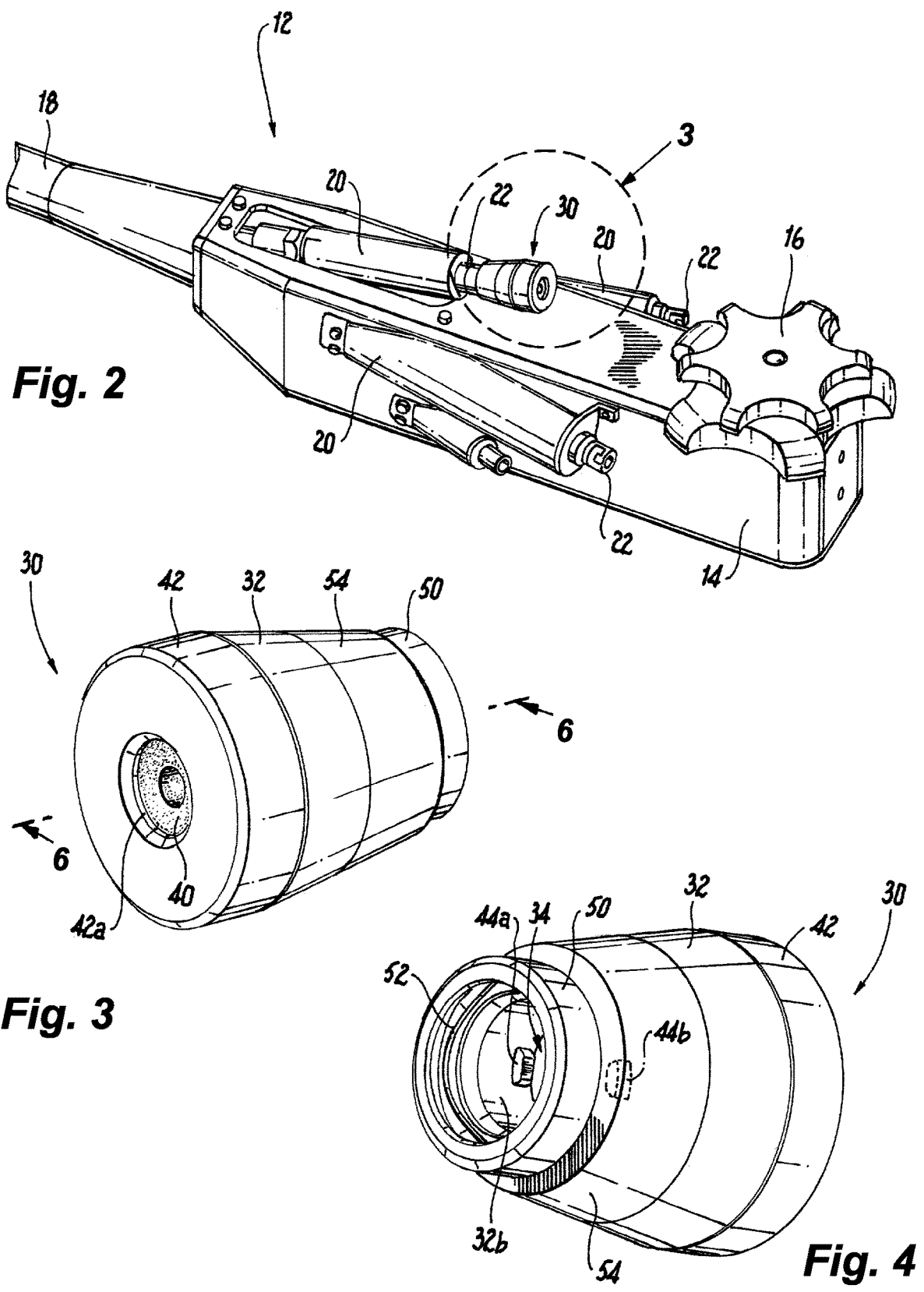
FIG. 2 is a localized perspective view of the robotic surgical device shown in FIG. 1, with the valve assembly of the subject disclosure engaged on a working channel of the robotic surgical device.
FIG. 3. is a perspective view of the valve assembly of the subject disclosure, viewed from a proximal end of the valve assembly.
FIG. 4. is a perspective view of the valve assembly of the subject disclosure, viewed from a distal end of the valve assembly.

Referring to FIG. 2, the overtube assembly 12 includes a housing 14 supporting a manual control mechanism 16 for manually controlling or otherwise steering the flexible overtube 18 that extends distally from the housing 14. A plurality of primary working channels 20 are operatively associated with the housing 14, each communicating with a respective interior lumen of the flexible overtube 18, which are not shown here. The primary working channels 20 of housing 14 are adapted to accommodate the passage of a robotically controlled surgical instrument, a videoscope or a similar endoscopic device into the flexible overtube 18 for introduction and use at a surgical site. Each primary working channel 20 has a proximal connector portion 22 for mechanically engaging with a valve assembly 30 that is constructed in accordance with the subject disclosure, as described in more detail below.

Referring now to FIGS. 3 through 6, the valve assembly 30 of the subject disclosure is a single-use, disposable component made primarily from biocompatible plastic materials and designed for use with the overtube assembly 12 throughout the duration of a surgical procedure. The valve assembly 30 is constructed from a plurality of components or parts that are joined together using known mechanical joining techniques. These components or parts include a valve body 32 having a longitudinal axis extending therethrough from a proximal end portion 32a of the valve body 32 to a distal end portion 32b of the valve body 32. The valve body 32 defines an axial bore 34 that includes an interior valve chamber 36 formed within the proximal end portion 32a of the valve body 32.

A valve seal 38 is situated within the interior valve chamber 36 of the valve body 32 for sealing the primary working channel 20 of the overtube assembly 12. An engagement mechanism 35, which is described in more detail below, is operatively associated with the distal end portion 32b of the valve body 32 for detachably connecting the valve assembly 30 to the proximal connector portion 22 of one of the primary working channels 20 of overtube assembly 12. The valve seal 38 has a cross-slit valve port 38a adapted to seal the primary working channel 20 of the overtube assembly 12 in the absence of an inserted instrument or videoscope. The valve seal 38 has a proximal flange 38b that seats on a shelf 32d defined in the interior valve chamber 36 of valve body 32.

A backup seal 40 is also situated within the interior valve chamber 36 of the valve body 32 proximal to the valve seal 38 for sealing against instrument videoscope insertion. The backup seal 40 is a septum seal that has a central port 40a adapted to seal against instrument or videoscope insertion. The valve assembly 30 further includes a proximal end cap 42 that is operatively associated with a proximal extension 32c of the valve body 32 for securing the backup seal 40 and the valve seal 38 within the interior chamber 36 of the valve body 32. The proximal end cap 42 of valve assembly 30 has a central access port 42a for receiving a surgical instrument, a videoscope or the like. The proximal end cap 42 further includes a distally projecting flange 42b for reception within a complementary channel 40b formed in the proximal surface of the backup seal 40.

Figure 5:
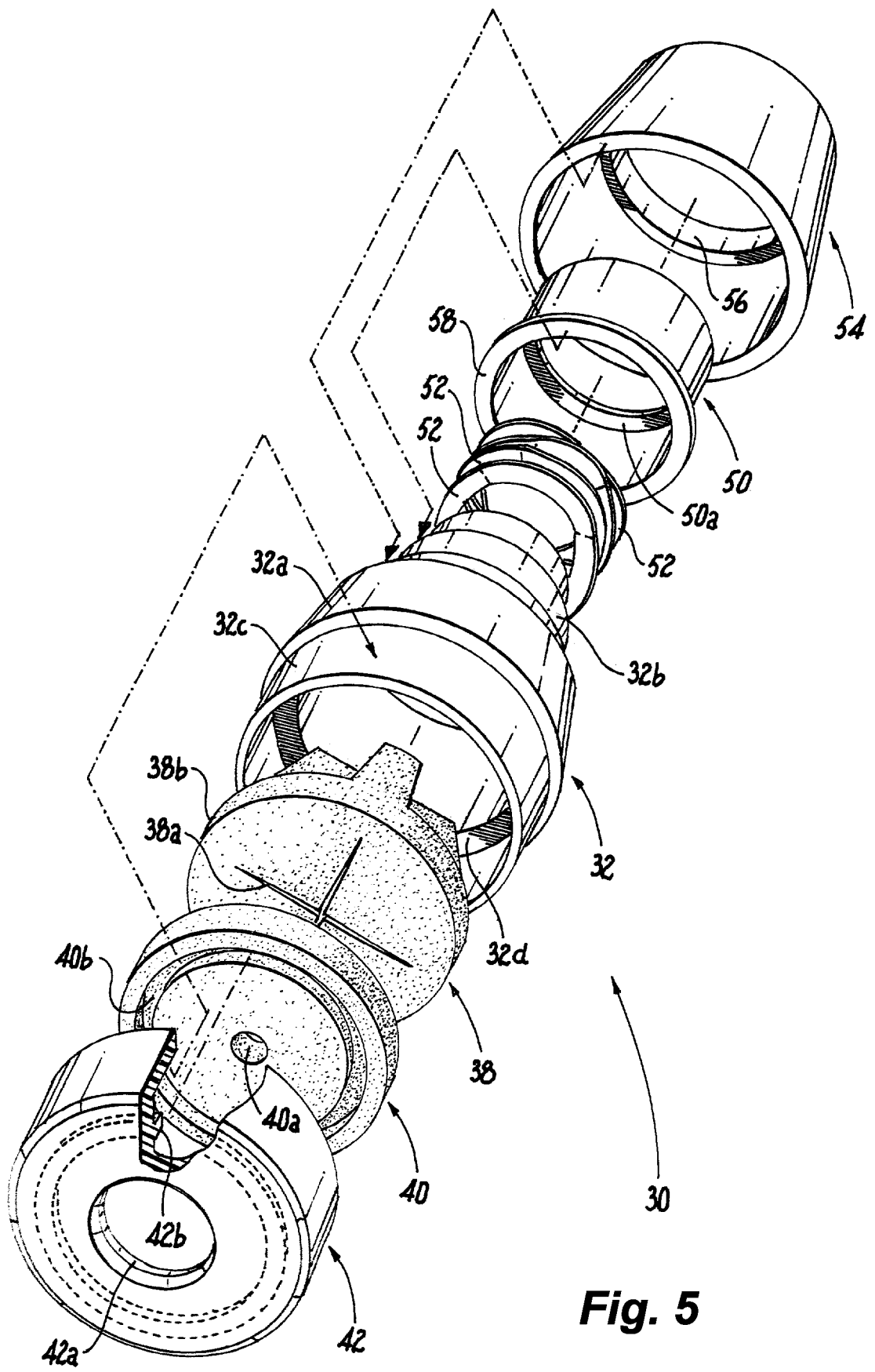
FIG. 5 is an exploded perspective view of the valve assembly of the subject disclosure with parts separated for ease of illustration.
Figure 6:
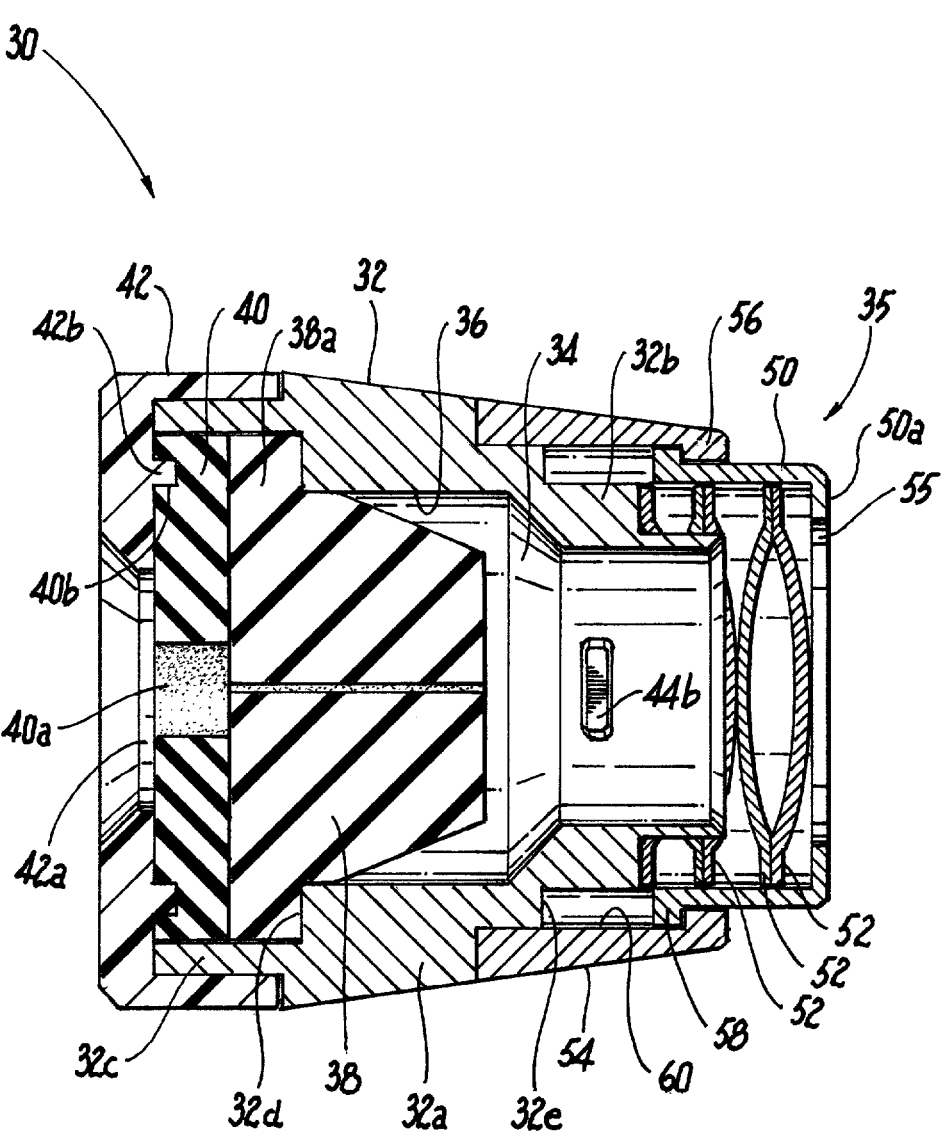
FIG. 6 is a side elevational view of the valve assembly of the subject disclosure taken along line 6-6 of FIG. 3.

Referring to FIGS. 5 and 6 in conjunction with FIGS. 7 through 10, the engagement mechanism 35 of valve assembly 30 is a bayonet-type engagement mechanism for detachably engaging the valve assembly 30 to the proximal connector portion 22 of the primary working channel 20 of the overtube assembly 12. The bayonet-type engagement mechanism 35 includes a pair of diametrically opposed locking tabs 44a and 48b (see FIG. 4), which extend radially inwardly into the axial bore 36 of the valve body 32 for cooperating with a pair of corresponding J-shaped engagement slots 48a and 48b (see FIG. 7) formed on the proximal connector portion 22 of each working channel 20 of the overtube assembly 12.

Figures 7, 8, 9, 10:
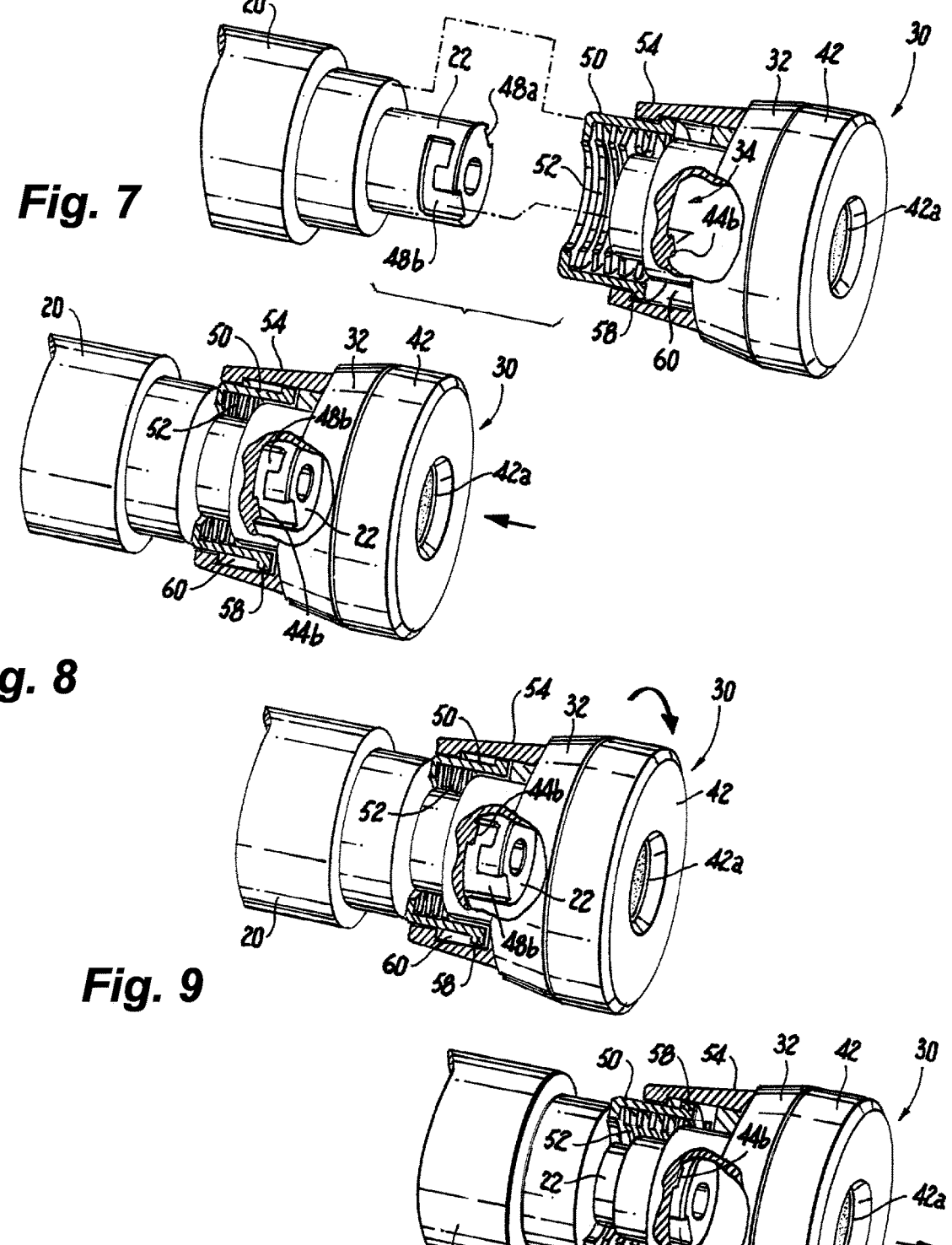
FIG. 7 is a perspective view of the valve assembly of the subject disclosure being aligned for engagement with the connector of the instrument channel of the robotic surgical device.
FIG. 8 is a perspective view of the valve assembly of the subject disclosure being pushed onto the connector of the instrument channel of the robotic surgical device.
FIG. 9 is a perspective view of the valve assembly of the subject disclosure being rotated into an engaged position on the connector of the instrument channel of the robotic surgical device.
FIG. 10 is a perspective view of the valve assembly of the subject disclosure being biased into an engaged position on the connector of the instrument channel of the robotic surgical device.

The bayonet-type engagement mechanism 35 of valve assembly 30 further includes a spring-biased crown 50 configured for axial movement between a first position biased distally relative to the distal end portion 32b of the valve body 32 (see FIGS. 6 and 7) and a second position retracted proximally relative to the distal end portion 32b of the valve body 32 (see FIG. 9). The spring-biased crown 50 has a central aperture 55 for receiving the proximal connector portion 22 of the primary working channel 20, and it is biased distally by a set of annular wave springs 52 positioned between the distal end portion 32*b* of the valve body 32 and the spring-biased crown 50. The set of annular wave springs 52 are best seen in FIGS. 5 and 6, and they are captured within the crown 50 by a radially inwardly extending end wall 50*a*. Those skilled in the art will readily appreciate that other types of biasing mechanisms or springs can be used as an alternative to the wave springs 52.

With continuing reference to FIGS. 5 and 6, the valve assembly 30 further includes a distal end cap 54 that has a radially inwardly extending annular flange 56 for capturing the radially outwardly extending flange 58 of the spring biased crown 50 relative to the distal end portion 32*b* of the valve body 32. More particularly, during the axial movement of the spring biased crown 50, which is illustrated in FIG. 8, the annular flange 58 travels within an annular gap 60 defined between the interior wall of the distal end cap 54 and the exterior wall of the distal end portion 32*b* of the valve body 32. The proximal extent of the axial travel of end cap 54 within the annular gap 60 is limited by surface 32*e*, best seen in FIG. 6.

Referring now to FIGS. 7 through 10, to install or otherwise mechanically engage the valve assembly 30 on the proximal connector portion 22 of the primary working channel 20 of the overtube assembly 12, the diametrically opposed locking tabs 44*a*, 44*b* of the valve assembly 30 are aligned with the corresponding diametrically opposed J-shaped engagement slots 48*a*, 48*b* of connector portion 22, as illustrated in FIG. 7. Then, an axially directed force is applied to the proximal end cap 42, causing the crown 50 to compress springs 52 as the flange 58 of crown 50 translates within the annular gap 60, until it reaches the extent of its travel against surface 32*e*, as depicted in FIG. 8.

Thereafter, as shown in FIG. 9, the valve assembly 30 is rotated in a clockwise direction about its central axis relative to the proximal connector portion 22 of the primary working channel 20, as illustrated in FIG. 9. As a result, the opposed locking tabs 44*a*, 44*b* of valve assembly 30 travel arcuately within the corresponding J-shaped slots 48*a*, 48*b* in proximal connector portion 22. Then, when the axial force applied to the valve assembly 30 is released, the wave springs 52 bias the valve assembly 30 in a proximal direction, as shown in FIG. 10.

As a result, the opposed locking tabs 44*a*, 44*b* of valve assembly 30 are positively engaged and retained within the corresponding J-shaped slots 448*a*, 48*b* of the connector portion 22, thereby securing the valve assembly 30 on the primary working channel 20. At such a time, the primary working channel 20 is advantageously sealed against instrument or videoscope insertion by the valve seal 38 and septum seal 40. After the surgical procedure is concluded and all instruments and videoscope have been withdrawn from the overtube assembly 12, each valve assembly 30 can be readily removed from the proximal connector portion 22 of each primary working channel 20 and discarded.

While the subject disclosure has been shown and described with reference to preferred embodiments, those skilled in the art will readily appreciate that changes and/or modifications may be made thereto without departing from the scope of the subject disclosure.

What is claimed is:

1. A valve assembly for sealing an instrument channel of a robotic surgical device, comprising:
   a) a valve body having a longitudinal axis extending therethrough from a proximal end portion of the valve body to a distal end portion of the valve body, and defining an axial bore including an interior valve chamber formed in the proximal end portion of the valve body;
   b) a valve seal situated within the interior valve chamber of the valve body for sealing the instrument channel of the robotic surgical device; and
   c) an engagement mechanism operatively associated with the distal end portion of the valve body for detachably connecting the valve assembly to the instrument channel of the robotic surgical device,
   wherein the engagement mechanism is a bayonet-type engagement mechanism for detachably engaging the valve assembly to the instrument channel of the robotic surgical device,
   wherein the bayonet-type engagement mechanism includes locking tabs that extend radially inwardly into the axial bore of the valve body for cooperating with corresponding engagement slots formed on a connector of the instrument channel of the robotic surgical device,
   wherein the bayonet-type engagement mechanism further includes a spring-biased crown configured for axial movement between a first position biased distally relative to the distal end portion of the valve body and a second position retracted proximally relative to the distal end portion of the valve body.

2. The valve assembly of claim 1, wherein the valve seal is a cross-slit valve seal adapted to seal the instrument channel of the robotic surgical device in the absence of an inserted instrument.

3. The valve assembly of claim 2, further comprising a backup seal situated within the interior valve chamber of the valve body proximal to the valve seal for sealing against instrument insertion.

4. The valve assembly of claim 3, wherein the backup seal is a septum seal adapted to seal against instrument insertion.

5. The valve assembly of claim 3, further comprising a proximal end cap operatively associated with the proximal end portion of the valve body for securing the backup seal and the valve seal within the interior chamber of the valve body.

6. The valve assembly of claim 1, wherein the bayonet-type engagement mechanism includes a pair of diametrically opposed locking tabs that extend radially inwardly into the axial bore of the valve body for cooperating with a pair of corresponding engagement slots formed on a connector of the instrument channel of the robotic surgical device.

7. The valve assembly of claim 1, wherein the spring-biased crown is biased distally by a wave spring positioned between the distal end portion of the valve body and the spring-biased crown.

8. The valve assembly of claim 7, further comprising a distal end cap for capturing the spring biased crown relative to the distal end portion of the valve body.

9. A disposable valve assembly for sealing an instrument channel of a robotic surgical device comprising:
   a) a valve body having a longitudinal axis extending therethrough from a proximal end portion of the valve body to a distal end portion of the valve body, and defining an axial bore including an interior valve chamber in the proximal end portion of the valve body;
   b) a cross-slit valve seal situated within the interior valve chamber of the valve body for sealing the instrument channel of the robotic surgical device;
   c) a septum seal situated within the interior valve chamber of the valve body proximal to the cross-slit valve seal for sealing against instrument insertion; and d) a bayonet-type engagement mechanism operatively associated with the distal end portion of the valve body for detachably connecting the valve assembly to a connector of the instrument channel of the robotic surgical device, wherein the bayonet-type engagement mechanism includes locking tabs that extend radially inwardly into the axial bore of the valve body for cooperating with corresponding engagement slots formed on the connector of the instrument channel of the robotic surgical device, wherein the bayonet-type engagement mechanism further includes a spring-biased crown configured for axial movement between a first position biased distally relative to the distal end portion of the valve body and a second position retracted proximally relative to the distal end portion of the valve body.

10. The disposable valve assembly of claim 9, further comprising a proximal end cap operatively associated with the proximal end portion of the valve body for securing the septum seal and the cross-slit valve seal within the interior chamber of the valve body.

11. The disposable valve assembly of claim 9, wherein the bayonet-type engagement mechanism includes a pair of diametrically opposed locking tabs that extend radially inwardly into the axial bore of the valve body for cooperating with a pair of corresponding engagement slots formed on the connector of the instrument channel of the robotic surgical device.

12. The disposable valve assembly of claim 9, wherein the spring-biased crown is biased distally by a wave spring positioned between the distal end portion of the valve body and the spring-biased crown.

13. The disposable valve assembly of claim 9, further comprising a distal end cap for capturing the spring-biased crown relative to the distal end portion of the valve body.

14. A disposable valve assembly for sealing an instrument channel of a robotic surgical device comprising:

a) a valve body having a longitudinal axis extending therethrough from a proximal end portion of the valve body to a distal end portion of the valve body, and defining an axial bore including an interior valve chamber in the proximal end portion of the valve body;

b) a valve seal situated within the interior valve chamber of the valve body for sealing the instrument channel of the robotic surgical device; and c) a bayonet-type engagement mechanism operatively associated with the distal end portion of the valve body for detachably connecting the valve assembly to a connector of the instrument channel of the robotic surgical device and including a pair of diametrically opposed locking tabs that extend radially inwardly into the axial bore of the valve body for cooperating with a pair of corresponding engagement slots formed on the connector of the instrument channel of the robotic surgical device wherein the bayonet-type engagement mechanism further includes a spring-biased crown configured for axial movement between a first position biased distally relative to the distal end portion of the valve body by a spring and a second position retracted proximally relative to the distal end portion of the valve body against the bias of the spring.

15. The disposable valve assembly of claim 14, wherein the bayonet-type engagement mechanism further includes a spring-biased crown configured for axial movement between a first position biased distally relative to the distal end portion of the valve body by a wave spring and a second position retracted proximally relative to the distal end portion of the valve body against the bias of the spring is a wave spring.

16. The disposable valve assembly of claim 14, further comprising a distal end cap for capturing the spring-biased crown and the wave spring relative to the distal end portion of the valve body.

17. The disposable valve assembly of claim 14, further comprising a septum seal situated within the interior valve chamber of the valve body proximal to the valve seal for sealing against instrument insertion.

18. The disposable valve assembly of claim 17, further comprising a proximal end cap operatively associated with the proximal end portion of the valve body for securing the septum seal and the valve seal within the interior chamber of the valve body.

19. The disposable valve assembly of claim 14, wherein the bayonet-type engagement mechanism includes a pair of diametrically opposed locking tabs that extend radially inwardly into the axial bore of the valve body for cooperating with a pair of corresponding engagement slots formed on the connector of the instrument channel of the robotic surgical device.

* * * * *